United States Patent
Lee et al.

(10) Patent No.: US 10,023,888 B2
(45) Date of Patent: Jul. 17, 2018

(54) MICROORGANISM FOR PRODUCING L-GLUTAMINE AND METHOD FOR PRODUCING L-GLUTAMINE USING SAME

(71) Applicant: CJ CHEILJEDANG CORPORATION, Seoul (KR)

(72) Inventors: Jin Nam Lee, Seoul (KR); Seung Hee Back, Seoul (KR); Jin Seok Sung, Yongin-si (KR); Tae Ho Song, Seoul (KR); Ha Dong Woo, Goyang-si (KR); Kyung Chang Lee, Seoul (KR); Jae Woo Jang, Hwaseong-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 15/515,744

(22) PCT Filed: Sep. 22, 2015

(86) PCT No.: PCT/KR2015/009909
§ 371 (c)(1),
(2) Date: Mar. 30, 2017

(87) PCT Pub. No.: WO2016/056773
PCT Pub. Date: Apr. 14, 2016

(65) Prior Publication Data
US 2017/0292135 A1    Oct. 12, 2017

(30) Foreign Application Priority Data

Oct. 8, 2014 (KR) .................. 10-2014-0135959

(51) Int. Cl.
| | | |
|---|---|---|
| C12N 1/20 | (2006.01) | |
| C12P 13/14 | (2006.01) | |
| C12P 13/00 | (2006.01) | |
| C12N 1/00 | (2006.01) | |
| C07K 14/245 | (2006.01) | |
| C12N 15/63 | (2006.01) | |
| C12P 13/04 | (2006.01) | |

(52) U.S. Cl.
CPC .......... *C12P 13/14* (2013.01); *C07K 14/245* (2013.01); *C12N 1/20* (2013.01); *C12N 15/63* (2013.01); *C12P 13/04* (2013.01); *C12N 1/00* (2013.01); *C12P 13/00* (2013.01)

(58) Field of Classification Search
CPC ........... C12P 13/14; C12P 13/04; C12P 13/00; C12N 1/00
See application file for complete search history.

(56) References Cited

U.S. PATENT DOCUMENTS

| | | | |
|---|---|---|---|
| 3,886,039 | A | 5/1975 | Yoshinaga et al. |
| 2010/0184163 | A1 | 7/2010 | Hayashi et al. |

FOREIGN PATENT DOCUMENTS

| | | |
|---|---|---|
| CN | 1710066 A | 12/2005 |
| EP | 1334176 | 8/2003 |
| JP | 197817675 | 2/1978 |
| JP | 1980148094 A | 11/1980 |
| JP | 1990186994 A | 7/1990 |
| JP | 1992088994 A | 3/1992 |
| JP | 2007244392 A | 9/2007 |
| JP | 5064396 B2 | 8/2012 |
| KR | 100015441 B1 | 6/1983 |
| KR | 100048440 B1 | 10/1991 |
| KR | 1020050018797 A | 2/2005 |
| KR | 1020130082124 A | 7/2013 |
| KR | 1020140087201 A | 7/2014 |
| RU | 2230114 C2 | 6/2004 |
| WO | 2008026698 A1 | 3/2008 |
| WO | 2011083859 A1 | 7/2011 |

OTHER PUBLICATIONS

Gerhardt, et al., Manual of Methods for General Bacteriology, American Society for Bacteriology. Washington D.C., USA, 1981. Books Review p. 1069 (with Related Material). Please be advised the methodology for general hacteriology was disclosed in Manual of Methods for General Bacteriology.
International Search Report for International Application No. PCT/KR2015/009909 dated Jan. 26, 2016.
Liu, et al., Microbial production of L-glutamate and L-glutamine by recombinant Corynebacterium glutamicum harboring Vitreoscilla hemoglobin gene vgb, Applied Genetics and Molecular Biotechnology, Appl Microbiol Biotechnol (2008) vol. 77, pp. 1297-1304.
Written Opinion for International Application No. PCT/KR2015/009909 dated Jan. 26, 2016.
Extended European Search Report dated Feb. 5, 2018, of the European Patent Application No. 15848984.9.
Takashi Hirasawa et al., L-Glutamate production by lysozyme-sensitive Corynebacterium glutamicum ItsA mutant strains, 2001, Research article, 5 pages, BMC Biotechnology.
Russian Office Action for Application No. 2017109400 dated Mar. 29, 2018, citing the above reference(s).
Japanese Office Action for Application No. 2017-517032 dated May 22, 2018, citing the above reference(s). In conformance with MPEP 609—Concise explanation of the relevance includes issue date of JP OA and references cited therein.

*Primary Examiner* — Delia Ramirez
(74) *Attorney, Agent, or Firm* — Cantor Colburn LLP

(57) ABSTRACT

Provided are a *Corynebacterium glutamicum* mutant that is resistant to high concentrations of L-glutamine, and a method of producing L-glutamine by using the mutant.

4 Claims, No Drawings

MICROORGANISM FOR PRODUCING L-GLUTAMINE AND METHOD FOR PRODUCING L-GLUTAMINE USING SAME

TECHNICAL FIELD

The present disclosure relates to a microorganism which produces L-glutamine, and a method of producing L-glutamine by using the microorganism.

BACKGROUND ART

L-glutamine, as an amino acid which is widely used in medicines, cosmetics, and health foods, has been produced mostly using compound-resistant or compound-sensitive microorganisms. For example, a sulfaguanidine-resistant strain (JP 1978-017675), an azaserine-resistant microorganism (JP 1980-148094), a penicillin-sensitive microorganism (JP 1992-088994), and a tyrosine-glutamic acid (tyr-glu)-resistant strain (JP 1990-186994) have been used for these purposes.

Under these circumstances, during research for development of strains with improved L-glutamine productivity, the present inventors found mutants having resistance to high concentrations of L-glutamine and a method of producing a high yield of L-glutamine by using the mutants, thus completing the present disclosure.

DETAILED DESCRIPTION OF THE INVENTION

Technical Problem

The present disclosure provides a *Corynebacterium glutamicum* mutant with improved L-glutamine productivity.

The present disclosure provides a method of producing L-glutamine by using the *Corynebacterium glutamicum* mutant.

Technical Solution

According to an aspect of the present disclosure, there is provided an L-glutamine-producing *Corynebacterium glutamicum* mutant that is resistant to L-glutamine.

As used herein, the term "L-glutamine" refers to the monoamide of glutamic acid, which is an amino acid which constitutes proteins and an L-amino acid having the formula of $H_2NCO-CH_2CH_2CH(NH_2)COOH$.

As used herein, the expression "resistant to L-glutamine" refers to a microorganism having properties of being able to grow, or being able to maintain or increase activity to produce L-glutamine, in an environment having a high concentration of L-glutamine.

When L-glutamine is accumulated in cells at a certain concentration or greater, this may induce inhibition by feedback regulation, lead to inhibition or suppression of the activity of glutamine synthetase, and consequently inhibit biosynthesis of L-glutamine. The feedback regulation by L-glutamine is released and the inhibition of L-glutamine synthesis does not work in a strain resistant to L-glutamine, such that the L-glutamine-resistant strain may produce L-glutamine under conditions of high concentrations of L-glutamine.

The mutant may be *Corynebacterium glutamicum* KCCM 11553P or *Corynebacterium glutamicum* KCCM11554P.

The mutant may have resistance to high concentrations of L-glutamine. For example, the mutant may have resistance to about 5 g/L to about 30 g/L of L-glutamine, and in some embodiments, about 15 g/L to about 30 g/L of L-glutamine, and in some other embodiments, about 20 g/L to about 25 g/L of L-glutamine.

The mutant may survive in a minimal medium containing about 15 g/L to about 25 g/L of L-glutamine for about 6 days or longer. For example, the mutant may survive for about 6 days or longer in a minimal medium (pH 7.0) containing about 15 g/L to about 25 g/L of L-glutamine, 0.1% of glucose, 0.04% of magnesium sulfate ($MgSO_4.7H_2O$), 0.1% of potassium dihydrogen phosphate ($KH_2PO_4$), 0.0001% of thiamine.HCl, 200 µg/L of biotin, and agar under incubation at about 30° C.

As used herein, the term "L-glutamine-producing microorganism" may refer to a microorganism inherently having the ability to produce L-glutamine or a microorganism with acquired glutamine productivity despite its parent strain lacking L-glutamine-producing ability.

In some embodiments, the *Corynebacterium glutamicum* mutant with improved L-glutamine-producing ability may be a mutant obtained by mutating a parent strain. Mutation of microorganisms may be performed by any of a variety of methods widely known in the art, for example, one of physical mutagenesis or chemical mutagenesis. For example, in the present disclosure, appropriate chemical mutation-inducing factors may include N-methyl-N'-nitro-N-nitrosoguanidine (NTG), diepoxybutane, ethyl methanesulfonate, mustard compounds, hydrazine, and nitrite. However, embodiments are not limited thereto. Non-limiting examples of physical mutation-inducing factors may include ultraviolet rays and gamma radioactive rays.

In some embodiments, to construct a mutant with improved L-glutamine-producing ability, a conventional glutamine-producing strain *Corynebacterium glutamicum* KFCC 10680 (disclosed in KR 10-0048440) may be used as a parent strain. After inducing random mutation in the parent strain *Corynebacterium glutamicum* KFCC 10680 with NTG, the resulting strain was cultured in a medium containing L-glutamine, and L-glutamine-producing abilities of the different stains were compared with each other to screen two mutants having resistance to L-glutamine. These two mutants were named Gln096 (KCCM 11553P) and Gln265 (KCCM 11554P), respectively. These *Corynebacterium glutamicum* mutants Gln096 and Gln265 were found to have an improved L-glutamine-producing ability with a higher yield of about 10% or greater than that of the parent strain.

According to another aspect of the present disclosure, a method of producing L-glutamine is provided, the method including culturing a *Corynebacterium glutamicum* mutant according to any of the above-described embodiments in a medium.

The *Corynebacterium glutamicum* mutant may be the same as described above, and will not be described herein.

The culturing may be performed using a suitable culture medium under suitable culturing conditions that are well known in the art. The culture medium and culturing conditions may be varied by one of ordinary skill in the art. For example, the culture medium may be a liquid medium. However, embodiments are not limited thereto. Example methods of the culturing may include batch culture, continuous culture, fed-batch culture, or a combination thereof. However, embodiments are not limited thereto.

The culture medium is required to have appropriate conditions for a specific, selected strain, and may also be appropriately varied by one of ordinary skill in the art. For example, the culture medium may be selected from various culture media for *Corynebacterium* strains disclosed in, for example, "*Manual of Methods for General Bacteriology*" (American Society for Bacteriology, Washington D.C., USA, 1981). However, embodiments are not limited thereto. The culture medium may include various carbon sources, nitrogen sources, and trace elements. Non-limiting examples of carbon sources available for the culture medium may include sugars and carbohydrates, such as glucose, sucrose, lactose, fructose, maltose, starch, and cellulose; oils and fats, such as soybean oil, sunflower oil, castor oil, and coconut oil; fatty acids, such as palmitic acid, stearic acid, and linoleic acid; alcohols, such as glycol and ethanol; and organic acids, such as acetic acid, wherein these carbon sources may be used individually or in combination. Non-limiting examples of nitrogen sources available for the culture medium are organic compounds, such as peptones, yeast extract, meat extract, malt extract, corn steep liquor (CSL), soybean flour, and urea; and inorganic compounds, such as ammonium sulfate, ammonium chloride, ammonium phosphate, ammonium carbonate, and ammonium nitrate, wherein these nitrogen sources may be used individually or in combination. Non-limiting examples of phosphorous sources available for the culture media may include potassium dihydrogen phosphate, dipotassium hydrogen phosphate, and corresponding sodium-containing salts. In some embodiments, the culture medium may include metal salts essential for growth, such as magnesium sulfate or iron sulfate. However, embodiments are not limited thereto. In some embodiments, the culture medium may further include amino acids and vitamins, which are essential for growth, in addition to the above-listed ingredients. In some embodiments, the culture medium may also include appropriate precursors. The culture medium or individual ingredients may be added to a culture solution in an appropriate manner, for example, in a batch or continuous manner. However, embodiments are not limited thereto.

In some embodiments, during the culturing, the pH of the culture solution may be adjusted by adding a compound, for example, ammonium hydroxide, potassium hydroxide, ammonia, phosphoric acid, or sulfuric acid into the culture solution for the selected microorganism in an appropriate manner. In some embodiments, during the culturing, foaming in the culture solution may be suppressed using an anti-foaming agent such as a fatty acid polyglycol ester. To keep the culture solution in an aerobic condition, oxygen or an oxygen-containing gas (for example, air) may be supplied into the culture solution. For example, the temperature of the culture solution may be maintained in a temperature range of about 20° C. to about 45° C., and in some embodiments, at a temperature of about 25° C. to about 40° C. For example, the culturing may be performed until a target quantity of L-glutamine is obtained, for example, for a culturing duration of about 10 hours to 160 hours.

The culturing may be performed in a culture medium containing a high concentration of L-glutamine, for example, about 15 g/L to about 25 g/L of L-glutamine, and in some embodiments, about 20 g/L to about 25 g/L of L-glutamine.

The method of producing L-glutamine may include recovering L-glutamine from the cultured microorganism or the cultured medium. The recovering of L-glutamine from the microorganism or the medium may be performed using an appropriate method known in the art according to the culturing method used, to thereby collect or recover the produced L-glutamine from the medium. Non-limiting examples of the method of recovering the produced L-glutamine may include centrifugation, filtration, anion-exchange chromatography, crystallization, and high-performance liquid chromatography (HPLC).

Advantageous Effects of the Invention

As described above, according to the one or more embodiments, L-glutamine may be produced by a *Corynebacterium glutamicum* mutant even in a medium containing a high concentration of L-glutamine. Therefore, a high yield of L-glutamine may be produced with high efficiency on an industrial production scale.

MODE OF THE INVENTION

One or more embodiments of the present disclosure will now be described in detail with reference to the following examples. However, these examples are only for illustrative purposes and are not intended to limit the scope of the one or more embodiments of the present disclosure.

Example 1: L-Glutamine-Producing Mutant Screening

To obtain microorganism mutants with improved glutamine-producing ability, mutation was induced in a microorganism in the following manner.

In particular, *Corynebacterium glutamicum* KFCC 10680 (*Corynebacterium glutamicum* KFCC 10680, see KR10-0048440) as a parent strain was cultured in an activation medium for about 16 hours (the activation medium containing 1% of beef extract, 1% of polypeptone, 0.5% of sodium chloride (NaCl), 0.5% of yeast extract, and 2% of agar and having a pH of 7.2, wherein each activation medium used in the examples had the same composition as that used in this example, and the percent unit (%) represents w/v %, which applies to all the examples). The resulting activated strain was cultured for about 14 hours in a seed culture previously sterilized at about 121° C. for 15 minutes, the seed culture (pH 7.0) containing 5.0% of glucose, 1% of bacto peptone, 0.25% of sodium chloride (NaCl), 1% of yeast extract, 3 μg/L of biotin, and 0.4% of urea, wherein every "seed culture" used in the examples had the same composition as that used in this example. 5 mL of the culture solution was added into a test tube and centrifuged at about 8,000 rpm for about 5 minutes, and the supernatant was removed. Then, a 100-mM citrate buffer was added into the test tube to re-suspend cell pellet, and the test tube was then centrifuged under the same conditions as above and the supernatant was removed therefrom to thereby wash the cells. 5 mL of the 100-mM citrate buffer was added into the test tube to re-suspend the cell pellet, and then N-methyl-N'-nitro-N-nitrosoguanidine (NTG) was added thereto to a final concentration of about 200 mg/L and left at room temperature for about 20 minutes. Next, the NTG-treated cells were centrifuged at about 8,000 rpm for about 5 minutes, the supernatant was removed, a 100-mM phosphate buffer was added to re-suspend the cell pellet, centrifugation was then performed under the same conditions as above, and the supernatant was removed, to thereby wash the cells. Next, 5 mL of a seed culture was added to the resulting NTG-treated cell pellet to re-suspend the same. This suspension was smeared on a plate containing a minimal medium, the minimal medium (pH 7.0) containing 0.1% of glucose, 0.04% of magnesium sulfate ($MgSO_4 \cdot 7H_2O$), 0.1% of potassium dihydrogen phosphate ($KH_2PO_4$), 0.0001% of thiamine.HCl, 200 μg/L of biotin, and 1.5% of agar, wherein every "minimal medium" used in the examples had the same composition as that used in this example, and cultured at about 30° C. for about 6 days. An $OD_{600}$ value of the viable cells was then measured. As a result of counting the number of cells, the cell death rate was found to be about 85%.

The washed NTG-treated strain was smeared on a plate containing a minimal medium, the minimal medium containing L-glutamine (final concentration: 15 g/L), and cultured at about 30° C. for about 6 days. The viable cell colonies were selected to screen L-glutamine-resistant mutants. The screened L-glutamine-resistant mutants were inoculated with an inoculation loop into 25 mL of a glutamine production medium (pH 6.8) (containing 4.0% of glucose, 3.0% of ammonium chloride ($NH_4Cl$), 0.3% of soy protein acid hydrolyzate, 5% of calcium carbonate ($CaCO_3$), 0.1% of calcium chloride ($CaCl_2$), 0.05% of magnesium sulfate ($MgSO_4.7H_2O$), 0.15% of potassium dihydrogen phosphate ($KH_2PO_4$), 0.15% of dipotassium hydrogen phosphate ($K_2HPO_4$), 0.3% of urea, 2 mg/L of thiamine (Thiamine.HCl), 5 µg/L of biotin, 20 mg/L of ferrous sulfate ($FeSO_4.7H_2O$), 20 mg/L of manganese sulfate ($MnSO_4.H_2O$), and 12 mg/L of zinc sulfate ($ZnSO_4.7H_2O$), wherein every "glutamine production medium" used in the examples had this same composition) in an Erlenmeyer flask for shaking, and then cultured at about 30° C. for about 48 hours while shaking at about 200 rpm. As a control group, the parent strain was cultured under the same conditions. Two types of L-glutamine-resistant mutants that produced a 10% or greater yield of glutamine than that of the parent strain *Corynebacterium glutamicum* KFCC-10680 were selected from the cultured product.

The selected mutants were named *Corynebacterium glutamicum* Gln096 and *Corynebacterium glutamicum* Gln265, respectively, and were deposited in the Korean Culture Center of Microorganisms (KCCM) on Jul. 3, 2014 with Accession Nos. KCCM11553P and KCCM11554P.

Example 2: Comparison of Resistance to L-Glutamine Between L-Glutamine-Producing Mutants To compare resistance to L-glutamine between the mutants selected in Example 1, each of the parent strain (KFCC 10680), *Corynebacterium glutamicum* Gln096 (KCCM11553P), and *Corynebacterium glutamicum* Gln265 (KCCM11554P) was smeared on plates containing a minimal medium containing respectively 2.5 g/L, 10 g/L, 15 g/L, 20 g/L, and 25 g/L of L-glutamine (on a final concentration basis) and incubated at about 30° C. for about 6 days.

As a result, as shown in Table 1, the parent strain exhibited poor growth at an L-glutamine concentration of 15 g/L and did not grow at an L-glutamine concentration of g/L or greater, while the mutants *Corynebacterium glutamicum* Gln096 (KCCM11553P) and *Corynebacterium glutamicum* Gln265 (KCCM11554P) still exhibited high growth at an L-glutamine concentration of 15 g/L and grew even at an L-glutamine concentration of 20 g/L or higher, indicating resistance of the mutants to high concentrations of L-glutamine.

TABLE 1

Comparison of resistance to L-glutamine

| Strain | L-glutamine concentration (g/L) | | | | |
|---|---|---|---|---|---|
| | 2.5 | 10 | 15 | 20 | 25 |
| KFCC 10680 | +++ | +++ | + | − | − |
| Gln096 | +++ | +++ | +++ | ++ | + |
| Gln265 | +++ | +++ | +++ | ++ | + |

+: grown/−: not grown; after incubation at about 30° C. for 6 days

Example 3: L-Glutamine Productivity Evaluation of L-Glutamine-Producing Mutants

To evaluate L-glutamine productivities of the mutants *Corynebacterium glutamicum* Gln265 (KCCM11554P) and *Corynebacterium glutamicum* Gln096 (KCCM11553P) obtained in Example 1, these mutants were cultured in the following manner to produce L-glutamine.

20 mL of a fermentation medium (pH 6.8) (containing 10% of glucose, 4.5% of ammonium chloride ($NH_4Cl$), 0.5% of soy protein acid hydrolyzate, 5% of calcium carbonate ($CaCO_3$), 0.1% of calcium chloride ($CaCl_2$), 0.05% of magnesium sulfate ($MgSO_4.7H_2O$), 0.15% of potassium dihydrogen phosphate ($KH_2PO_4$), 0.15% of dipotassium hydrogen phosphate ($K_2HPO_4$), 0.3% of urea, 2 mg/L of thiamine (thiamine.HCl), 5 µg/L of biotin, 20 mg/L of ferrous sulfate ($FeSO_4.7H_2O$), 20 mg/L of manganese sulfate ($MnSO_4.H_2O$), and 12 mg/L of zinc sulfate ($ZnSO_4.7H_2O$), wherein every "fermentation medium" used in the examples had the same composition) was added into a 250-mL Erlenmeyer flask for shaking, and sterilized at about 121° C. for about 15 minutes. The parent strain *Corynebacterium glutamicum* KFCC10680, and the mutants *Corynebacterium glutamicum* Gln265 (KCCM11554P) and *Corynebacterium glutamicum* Gln096 (KCCM11553P) were cultured in an activation medium at about 30° C. for about 16 hours, respectively. Each of the resulting activated strains (KFCC10680, Gln096, and Gln265) was inoculated into the fermentation medium with an inoculation loop and cultured at about 30° C. for about 48 hours with shaking at about 200 rpm. After completion of the culturing, the concentration of L-glutamine present in the supernatant of each of the media from which cells were removed was measured using a YSI 7100 Multiparameter Bioanalytical System (available from YSI Inc.). The results are shown in Table 2.

TABLE 2

| Strain | L-glutamine concentration (g/L) |
|---|---|
| KFCC10680 | 12.6 |
| Gln096 (mutant) | 13.8 |
| Gln265 (mutant) | 14.1 |

Referring to Table 2, the parent strain *Corynebacterium glutamicum* KFCC10680 produced about 12.6 g/L of L-glutamine, while the mutant *Corynebacterium glutamicum* Gln096 produced about 13.8 g/L of L-glutamine, according to an embodiment, with an increased L-glutamine productivity of about 9.5% or greater, as compared with that of the parent strain. The mutant *Corynebacterium glutamicum* Gln265 produced about 14.1 g/L of L-glutamine, according to an embodiment, with an increased L-glutamine productivity of about 11% or greater, as compared with that of the parent strain.

Depositary Institution: Korean Culture Center of Microorganisms (KCCM) (International Depositary Authority)

Accession No.: KCCM11553P

Date of deposit: 20140703

Depositary Institution: Korean Culture Center of Microorganisms (KCCM) (International Depositary Authority)

Accession No.: KCCM11554P

Date of deposit: 20140703

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

The invention claimed is:

1. A *Corynebacterium glutamicum* mutant KCCM11553P or KCCM11554P producing L-glutamine and having resistance to L-glutamine.

2. The *Corynebacterium glutamicum* mutant KCCM11553P or KCCM11554P of claim 1, wherein the *Corynebacterium glutamicum* mutant KCCM11553P or KCCM11554P is able to survive in a culture medium containing about 15 g/L to about 25 g/L of L-glutamine for about 6 days or longer.

3. A method of producing L-glutamine, the method comprising culturing the *Corynebacterium glutamicum* mutant of claim 1 in a medium, and recovering L-glutamine from the mutant of the medium.

4. A method of producing L-glutamine, the method comprising:

culturing the *Corynebacterium glutamicum* mutant of claim 2 in a medium, and recovering L-glutamine from the mutant of the medium.

* * * * *